(12) United States Patent
Houston et al.

(10) Patent No.: US 10,188,532 B2
(45) Date of Patent: Jan. 29, 2019

(54) BLOOD-FLOW TUBING

(71) Applicant: VASCULAR FLOW TECHNOLOGIES LIMITED, Dundee (GB)

(72) Inventors: John Graeme Houston, Tayside (GB); John Bruce Cameron Dick, Tayside (GB); Peter Stonebridge, Tayside (GB)

(73) Assignee: Vascular Flow Technologies Limited, Dundee (GB)

( * ) Notice: Subject to any disclaimer, the term of this patent is extended or adjusted under 35 U.S.C. 154(b) by 0 days.

(21) Appl. No.: 15/214,938

(22) Filed: Jul. 20, 2016

(65) Prior Publication Data

US 2016/0346101 A1 Dec. 1, 2016

Related U.S. Application Data

(63) Continuation of application No. 13/345,628, filed on Jan. 6, 2012, now Pat. No. 9,737,421.

(51) Int. Cl.
| A61F 2/06 | (2013.01) |
| A61F 2/844 | (2013.01) |
| A61F 2/86 | (2013.01) |
| A61F 2/90 | (2013.01) |

(52) U.S. Cl.
CPC .............. *A61F 2/844* (2013.01); *A61F 2/06* (2013.01); *A61F 2/86* (2013.01); *A61F 2/90* (2013.01); *A61F 2002/065* (2013.01); *A61F 2002/068* (2013.01); *A61F 2230/0017* (2013.01); *A61F 2230/0091* (2013.01); *Y10T 428/139* (2015.01); *Y10T 428/1352* (2015.01); *Y10T 428/1355* (2015.01); *Y10T 428/1362* (2015.01); *Y10T 428/1397* (2015.01)

(58) Field of Classification Search
CPC .. A61F 2/07; A61F 2/2418; A61F 2/82; A61F 2/06; A61F 2/88; A61F 2/95; A61F 2002/068; A61F 2/86; A61F 2/89; A61F 2002/072; A61F 2002/823
See application file for complete search history.

(56) References Cited

U.S. PATENT DOCUMENTS

| 1,974,110 A | 9/1934 | Higley |
| 3,457,762 A | 7/1969 | De Gain |
| 3,479,670 A | 11/1969 | Medell |
| 3,503,246 A | 3/1970 | Shiokawa |

(Continued)

FOREIGN PATENT DOCUMENTS

| EP | 0699424 B1 | 4/1995 |
| EP | 0699423 A2 | 6/1996 |

(Continued)

OTHER PUBLICATIONS

Stonebridge, P.A.; Spiral Laminar Flow In Vivo; Journal; Clinical Science; Edinburgh, U.K.; 5 pages; Sep. 25, 1995.

(Continued)

*Primary Examiner* — Ann Schillinger
(74) *Attorney, Agent, or Firm* — Bracewell LLP; Keith R. Derrington

(57) ABSTRACT

An artificial or modified natural blood flow tubing has a helical-flow inducer to induce helical flow in such a fashion as to eliminate or reduce turbulence. One inducer is a tubular stent of expansible mesh having a helical vane.

9 Claims, 3 Drawing Sheets

(56) References Cited

U.S. PATENT DOCUMENTS

| | | | |
|---|---|---|---|
| 3,606,780 A | 9/1971 | Nagahara | |
| 3,693,329 A | 9/1972 | Willis | |
| 3,746,126 A | 7/1973 | de Cardenas | |
| 3,750,444 A | 8/1973 | Bittner | |
| 4,514,997 A | 5/1985 | Zifferer | |
| 4,596,548 A | 6/1986 | DeVries et al. | |
| 4,629,458 A | 12/1986 | Pinchuk | |
| 4,658,892 A | 4/1987 | Shinohara et al. | |
| D290,752 S | 7/1987 | Inoue | |
| 4,743,480 A | 5/1988 | Campbell et al. | |
| 4,753,221 A | 6/1988 | Kensey et al. | |
| 4,892,539 A | 1/1990 | Koch | |
| D307,174 S | 4/1990 | Bjorkman et al. | |
| D326,031 S | 5/1992 | Walters et al. | |
| 5,116,350 A | 5/1992 | Stevens | |
| D327,879 S | 7/1992 | Lou | |
| 5,156,620 A | 10/1992 | Pigott | |
| D338,193 S | 8/1993 | Sasaki | |
| 5,238,642 A | 8/1993 | Benquet et al. | |
| 5,500,013 A | 3/1996 | Buscemi et al. | |
| D376,011 S | 11/1996 | Nunokawa | |
| 5,579,758 A | 12/1996 | Century | |
| 5,609,624 A | 3/1997 | Kalis | |
| 5,653,745 A | 8/1997 | Trescony et al. | |
| 5,824,212 A | 10/1998 | Brockhoff | |
| 5,989,230 A | 11/1999 | Frassica | |
| 6,071,305 A * | 6/2000 | Brown | A61F 2/82 606/191 |
| 6,261,312 B1 * | 7/2001 | Dobak, III | A61B 18/02 606/21 |
| 6,358,276 B1 * | 3/2002 | Edwin | A61F 2/82 604/500 |
| 6,500,186 B2 | 12/2002 | Lafontaine et al. | |
| 6,514,284 B1 | 2/2003 | Cheng | |
| 6,660,032 B2 | 12/2003 | Klumb et al. | |
| 7,114,524 B2 | 10/2006 | Houston et al. | |
| 7,185,677 B2 | 3/2007 | Houston et al. | |
| 7,331,989 B2 | 2/2008 | Houston et al. | |
| 2002/0179166 A1 | 12/2002 | Houston et al. | |
| 2003/0225453 A1 | 12/2003 | Murch | |
| 2006/0124187 A1 | 6/2006 | Houston et al. | |
| 2006/0265051 A1 | 11/2006 | Caro et al. | |

FOREIGN PATENT DOCUMENTS

| | | |
|---|---|---|
| EP | 0612536 B1 | 12/1999 |
| EP | 1254645 B1 | 4/2007 |
| EP | 1135171 B1 | 8/2008 |
| FR | 2657945 B3 | 1/1992 |
| GB | 0409528 | 5/1934 |
| GB | 0729618 | 5/1955 |
| GB | 2093943 B1 | 5/1984 |
| GB | 2092894 B | 3/1985 |
| WO | 1983003349 | 10/1983 |
| WO | 9012550 A1 | 11/1990 |
| WO | 9315661 A1 | 8/1993 |
| WO | 9520986 A1 | 8/1995 |
| WO | 9535072 A1 | 12/1995 |
| WO | 9724081 A1 | 7/1997 |
| WO | 9819632 A1 | 5/1998 |
| WO | 9826731 A1 | 6/1998 |
| WO | 9853764 A1 | 12/1998 |
| WO | 9955256 A1 | 11/1999 |
| WO | 200162185 A1 | 8/2001 |
| WO | 0189419 A1 | 11/2001 |

OTHER PUBLICATIONS

Stonebridge, P.A.; Spiral Laminar Flow in Arteries; The Lancet Journal; vol. 338; 2 pages; Nov. 30, 1991.

British Priority document GB 9828696.6 as filed in the British Patent Office on Dec. 29, 1998.

* cited by examiner

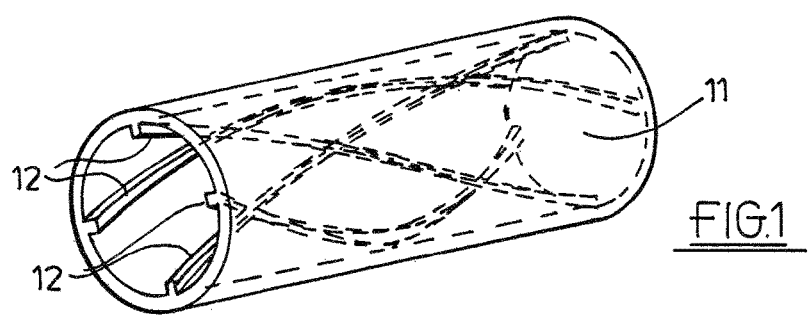
FIG. 1
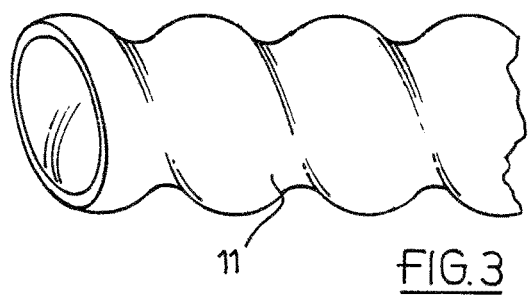
FIG. 3
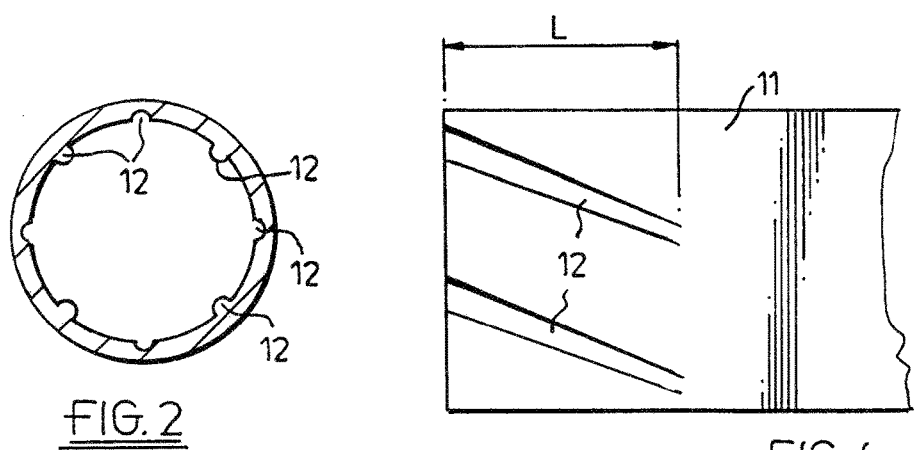
FIG. 2
FIG. 4
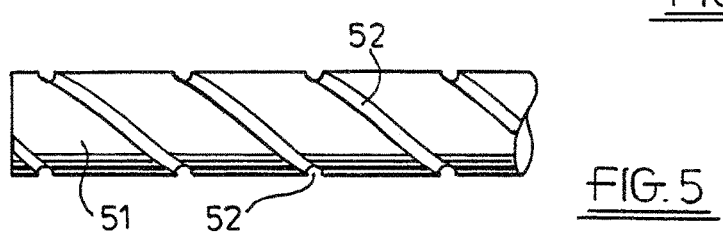
FIG. 5

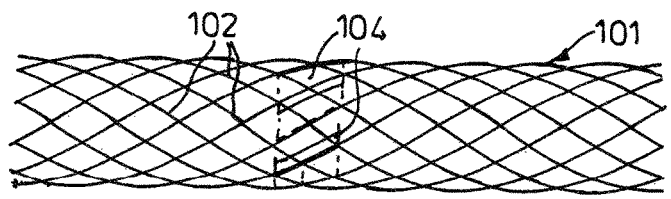
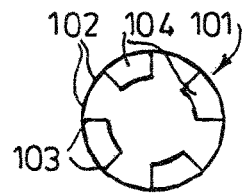
FIG.9  FIG.10
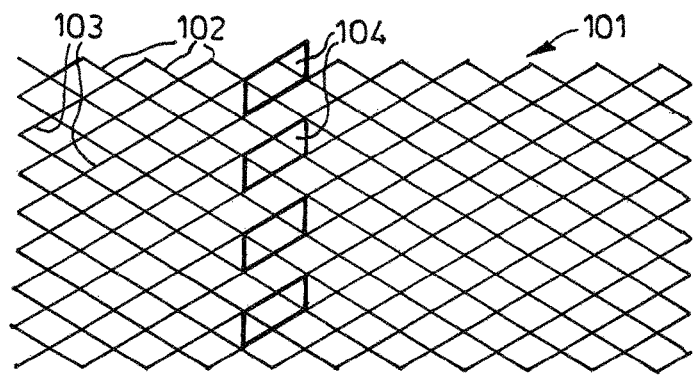
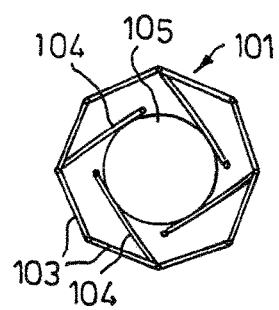
FIG.11  FIG.12
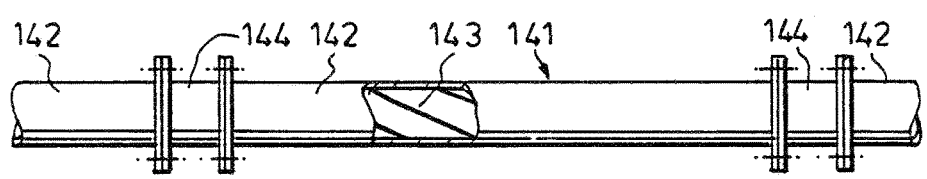
FIG.13
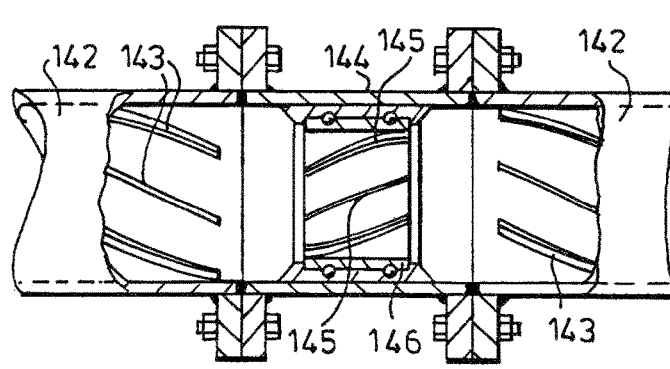
FIG.14

BLOOD-FLOW TUBING

CROSS REFERENCE TO RELATED APPLICATIONS

This application is a continuation of application Ser. No. 13/345,628, filed Jan. 6, 2012, which claimed priority to application Ser. No. 11/696,052, filed Apr. 3, 2007, which claimed priority to application Ser. No. 10/650,217, filed Aug. 9, 2003, which claimed priority to application Ser. No. 09/869,661, filed Jun. 29, 2001, which claimed priority from PCT No. PCT/GB99/04449, filed Dec. 23, 1999 which claimed priority from U.K. application Serial No. 9828686.6, filed Dec. 28, 1998, the full disclosures of which are incorporated by referenced herein and for all purposes.

BACKGROUND OF THE INVENTION

1. Field of Invention

This invention relates inter alia to artificial or modified natural blood-flow tubing, by which is meant artificial vascular prostheses or modified natural grafts or autografts, and tubing in which blood flows outside the body, e.g. in dialysis or in open heart surgery. Indeed, the invention might well extend to any tubing that carries a laminar flow, and particularly, but by no means exclusively, a pulsatile flow.

2. Description of Prior Art

Spiral flow has been observed (Stonebridge P. A. and Brophy C. M., 1991, Spiral laminar flow in arteries Lancet 338: 1360-61) during angioscopy, as has the presence of spiral folds on the endoluminal surface of blood-vessels. The observation, it was said could have been an artifact of angioscopy, or the phenomenon may occur only in diseased arteries because of turbulence generated atherosclerosis, or it may be physiological, the latter having some support from other observations of rotational flow.

Indeed, in this seminal article, it is remarked that, if confirmed, the existence of spiral rather than laminar blood flow in peripheral arteries would have striking implications for the understanding of haemodynamics, arterial wall function, the pathogenesis of atherosclerosis and intimal hyperplasia, and the design of prosthetic graft materials.

Confirmation came with the publication by Stonebridge and others of a paper "Spiral laminar flow in vivo" in Clinical Science (1996, 9: 17-21) in which, using standard color flow Döppler techniques, velocity information was obtained, from which a rotational element to forward flow during all or part of the pulse cycle was demonstrated in each of eleven healthy male volunteers.

However, even with this confirmation, it was admitted that it had not yet been shown whether angioscopic observations of a spiral pattern on the endoluminal surface of arteries and spiral flow patterns were real events or observational artefacts.

More recent work with magnetic resonance imaging ("MRI") has established, however, that rotational flow is beneficial at least in certain situations and is presumed, on that account, to be "selected for".

The prediction, therefore, by Stonebridge and Brophy in the 1991 Lancet report is vindicated, though it has only now become apparent just how to design prosthetic graft materials in order to reproduce, or at least not to destroy, the physiological rotation, and not at the same time bring about any disadvantages. It has also become apparent that the findings are of interest in connection with blood flow tubing other than grafts, and, indeed, with other tubing as well.

SUMMARY OF THE INVENTION

Described herein is an example of an intravascular stent which includes a tubular member, the tubular member having an internal helical formation to induce spiral-flow therethrough, wherein the tubular member can be a tubular mesh member, a tubular member formed from a wire or a tubular member of a mesh material that is formed from expanded sheet. In an example, the tubular member is expansible and is inserted by catheterization in collapsed form and which becomes expanded on release from the catheter, the internal helical formation being attached to an interior portion of the tubular member. The tubular mesh member can be formed from a wire and has crisscrossed wires extending helically around the periphery of the stent, and the internal helical formation comprises a helical vane member attached to such wires. The tubular mesh member, the wire, or the expanded sheet can be made from metal. Optionally, the wire can be a wire spring. In an example, the internal helical formation has a helix angle between 5 and 50 degrees relative to a longitudinal axis of the stent. In one alternate embodiment, the helix angle is between 5 and 16 degrees relative to the longitudinal axis of the tubular member. Further optionally, the helix angle can be about 16 degrees relative to the longitudinal axis of the tubular member. The helix angle of the internal helical formation is optionally adjustable. The internal helical formation can be a ridge. In another example, the internal helical formation is made up of a rigid support coaxially mounted within the tubular member, and a spiral flow inducer vane surrounding and extending from the rigid support. In one alternative example, the internal helical formation includes a rigid support rod coaxially mounted in the tubular member, a flexible sleeve within the tubular member and surrounding the support rod, a flexible helical vane mounted to the sleeve, and wherein the sleeve is axially contractible relative to the support rod to vary an angle of the vane relative to the support rod.

Another example of an intravascular stent is disclosed herein and which includes an expansible tubular member having a collapsed form to be inserted into a blood vessel and an expanded form to be retained within the blood vessel, the tubular member having at least one vane stationarilly attached to an interior thereof and extending helically to induce spiral flow of blood. The tubular member can be made from a plurality of wires that extend helically and cross each other to form junctions.

Tubing may be utilised to optimise mixing and exhaust of fluid. For example, the tubing design may encourage mixing so as to reduce sedimentation, or may beneficially affect the fluid flow pattern (eg. spiral) beyond the outlet of the tubing. The latter effect may be applied, for example, in tubing such as hoses and firehoses. Optimisation of tubing characteristics may result in a reduction of fluid noise at the exhaust or vibration in the tubing.

The term "tubing" as used here may include all types of conduit which transport or contain liquid or gaseous fluid, in both blood and non-blood fields. Tubing for the blood field may include, but is not restricted to, graft stems and giving sets.

Such tubing may have, as with blood flow tubing, internal helical ridging and/or grooving, and other attributes of the blood flow tubing above referred to. It may particularly be used in plant for delivering slurries or suspensions of solids in liquids, or, for example, as pipeline for delivering viscous liquids such as oils. It may have helical flow inducing means at least at interfaces with supply or storage vessels, and at branches.

The helical flow inducing means may have active flow rotating means, such for example as driven vanes, and such active flow rotating means may be situated at intervals, for example, along a pipeline.

BRIEF DESCRIPTION OF THE DRAWINGS

Some of the features and benefits of the present invention having been stated, others will become apparent as the description proceeds when taken in conjunction with the accompanying drawings, in which:

FIG. 1 is a perspective view of a short length of tubing of a first embodiment suitable for prosthetic implant in a cardio-vascular system;

FIG. 2 is a cross-section of a second embodiment of tubing;

FIG. 3 is a perspective view of a third embodiment;

FIG. 4 is a view of the inside of an example of a length of tubing, opened out;

FIG. 5 in an elevation of an example of a mandrel for use in casting tubing according to the invention;

FIG. 9 is a view of an example of a mesh material stent from the side, in its expanded condition;

FIG. 10 is an end-on view of the stent of FIG. 9;

FIG. 11 is an opened-out view of the stent of FIG. 10;

FIG. 12 is an end-on view, to a larger scale, of the stent of FIG. 11 in its collapsed condition, before release from the catheter;

FIG. 13 is a view of an example of a pipeline, with active helical-flow inducing means; and FIG. 14 is a section through the pipeline of FIG. 13.

Figure 6:
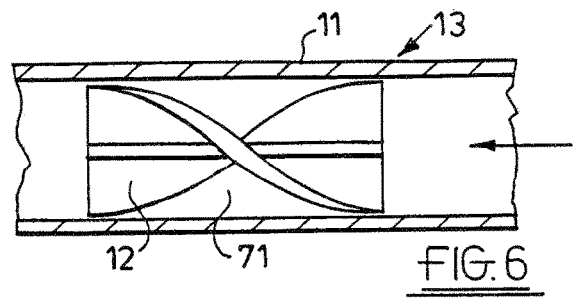
FIG. 6 is a view of an example of a vaned device in a tube.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

The drawings illustrate an example of blood-flow tubing 11 having helical-flow inducing means 12 adapted to induce helical flow in such fashion as to eliminate or reduce turbulence. The tubing 11 may be artificial, for example woven or knitted synthetic polymer fibre, in which the helical-flow inducing means may be knitted or woven structure as by three dimensional knitted or woven formation, or extruded or cast tubing, or modified natural, e.g. autograft material with an insert or with grooving made e.g. by a laser.

The helical-flow inducing means 12 may include grooving 14 and/or ridging 15, which may be multi-start grooving and/or ridging as seen in FIGS. 1, 2 and 4. Square-section ridging, as seen in FIG. 1, or grooving, or semi-circular section ridging and/or grooving, as seen in FIG. 2, can be used, but other cross-sections will serve as well, for example, triangular.

However, as seen in FIG. 3, a non-circular section tube 11 can have a twist, and may also have internal ridging and/or grooving. A twisted tube may be cast as such on a twisted mandrel or, if, for example, of thermoplastic material, may be twisted and heat-set in that state. Even a circular-section tube, bent into a corkscrew shape, can, if the dimensions are appropriate for the density, velocity and viscosity of the liquid flowing through it, give rise to a circulation in the flow.

The helical-flow inducing means 12 may extend over the whole length of the tubing 11. In an example, the helical-flow inducing means 12 is provided where turbulence is likely to occur, for example at the inlet or outlet from the tubing 11, or in branched tubing as seen in FIG. 9, where turbulence can be occasioned in the branch region and can be controlled by ridging and/or grooving 12 at the inlets to the two minor branches 11b where they join the main branch 11a, and/or in the main branch 11a itself. Optionally, different ridging and/or grooving can be in the two minor branches, where, for example, they run at different angles to the main branch.

It may be arranged that the ridging and/or grooving 12 has a reducing helix angle in the flow direction over at least part of its length—an example of which is illustrated in FIG. 4, where the grooving 12 is also tapered so as to extend only over an inlet region L, but the tapering and reducing angle could extend over longer lengths of tubing. The opposite-helix angle increasing and/or depth of grooving or height of ridging increasing in the flow direction may also be appropriate in some circumstances.

A designated helix angle, or range of helix angles, where increasing or decreasing angles are used, can depend on a number of factors, such as but not limited to, dimensions of the tubing 11, the density and viscosity of the liquid flowing through the tubing 11, and the velocity of the liquid flow. Examples exist where helix angles from about 5° to about 50°, including about 16°, induce a helical flow pattern in the fluid. Angles up to around 5° and greater than 50° can also induce helical flow patterns in the fluid.

FIG. 5 is an elevation of an example of mandrel 51 such as may be used in a coagulation casting process to make prosthesis of polyetherurethane or other biocompatible polymer. Grooves 52 are provided on the mandrel 51 which then forms a tube with internal ridging.

Figure 7:
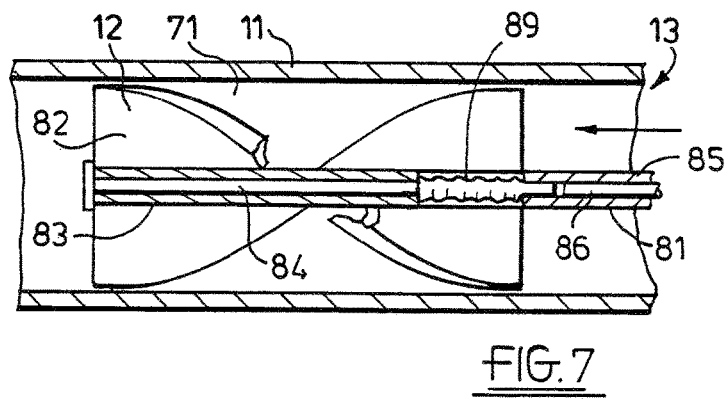
FIG. 7 is a view of a second example of a vaned device in a tube.
Figure 8:
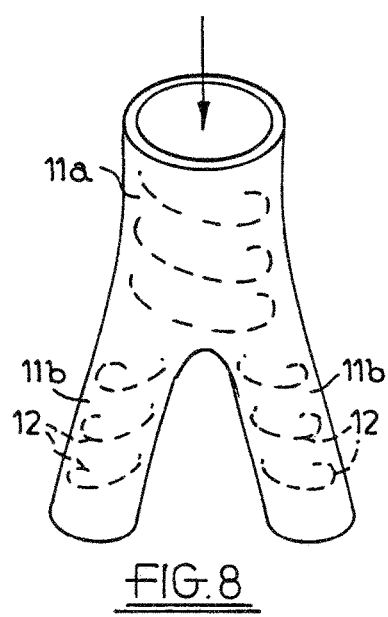
FIG. 8 is a view of an example of a branched tube according to the invention.

FIGS. 6 and 7 illustrate embodiments of helical vane devices 71 which can be inserted in tubing to cause helical flow of fluid flowing inside the tubing 11 and across the vane devices 71. In the example of FIG. 7 the helical flow effect can be increased by a probe 81, such as one used in angiography. The vanes 82 as shown are on a sleeve 83 and sufficiently flexible to be compressed on a rigid support 84 by a sleeve 85 of the probe 81 being advanced relative to a core 86, the core 86 engaging the support 84 while the sleeve 85 is advanced against the sleeve 83, the sleeve 83 being held in the compressed state by a ratchet arrangement 89 between support 84 and sleeve 83. Such a device may be adjusted during angiography while observing the rotational flow induced, thereby, e.g. by MRI. The adjustment may be effected in any other fashion, e.g. by the application of torque to one end while holding the other end fixed.

FIGS. 9 to 12 illustrate examples of an expansible mesh material stent 101 which is inserted by catheterisation. Such stents are sometimes made of a metal with a shape memory and are presented on a catheter in collapsed form, expanding on release from the catheter as they reach body temperature, others expand elastically as they are pushed from a captive surround. In one example of an expanded condition, as shown in FIGS. 9 and 10, the stent 101 is formed from a mesh cylinder formed, for example, of welded wires 102 with joined segments 103 extending helically around the periphery of the stent 101, though some stents are of expanded metal sheet, in which case the segments would be integral strips. Attached to some of the segments 102, on the inside of the stent 101, are examples of vane members 104. In a welded wire construction, these could be plates welded to segments, while in an expanded sheet construction, the vane members 104 could be parts of the sheet, leaving corresponding holes in the mesh. FIG. 11 shows an opened-out version of the stent 101, as if cut along a generator of the cylinder and laid flat, with the inside face uppermost. FIG. 12, which is to a larger scale, shows the stent 101 in collapsed form around a catheter wire 105, without, however, the associated surround which contains them for insertion and out from which they are pushed once maneuvered into position.

Aside from blood flow tubing for implantation, or devices for use in improving circulation, such as bypasses and stents, blood flow tubing is found in various items of medical equipment such as heart-lung machines, dialysis machines and blood transfusion equipment. Inasmuch as, in such equipment, blood flows much as it does in the body, it could be at least as important to fashion such tubing to give the best possible flow characteristics, in particular, the avoidance of thromboses being generated during prolonged use of the equipment, as in heart surgery and dialysis, and the principles set out above in relation to natural and artificial grafts can also be applied to such external blood flow tubing. Even in giving sets, where flow rate is likely to be low, helical flow may well be found to have advantages, especially at the interfaces between tubing and cannulae and flow regulators.

FIGS. 13 and 14 illustrate, by way of example, the application of the notion of helical flow to an oil pipeline 141. The pipeline 141 is itself made up from pipe sections 142, which may themselves have internal helical grooving and/or ridging 143. In an optional embodiment, active flow rotating means 144 are provided at intervals along the pipeline 141, at junctions between pipe sections 142. The active flow rotating means include, as seen in FIG. 13, rotary vanes 145 mounted in connecting rings 146. Depending on circumstances, it may be desirable to drive the vanes by external means, such, for example, as a motor, which can be, for example, solar powered, or it may be preferred to derive power for rotating the vanes from the flow itself, the general idea being to refresh any swirl component that might have attenuated over the preceding pipe section.

In addition to pipelines, the idea of helical flow will clearly be of benefit in plant in which slurries and suspensions of solids in liquids are transported between reactors and storage tanks, for instance. Examples of such plants are food producing plants, where soups, sauces and like products are manufactured.

It is noted that the mere provision of helical flow induction will not necessarily reduce or eliminate turbulence. It will be important to select the most appropriate configuration, which may well be done by trial and error. It may, of course, be found, especially where sharp bends or corners are encountered in the tubing, that there is a limit to the stability of rotational flow—it may be desirable, if possible, to refashion the tubing to eliminate sharp bends or corners before helical flow will have the effect of inducing or maintaining non-turbulent flow.

Designs for the tubing and methods for making the same other than those already discussed can of course be envisioned, all falling within the scope of the invention.

What is claimed is:

1. An intravascular stent comprising:
   a tubular member having an internal surface and an external surface,
   wherein the tubular member has an internal helical formation to induce spiral-flow therethrough, and wherein the internal helical formation is provided on a portion of the internal surface and the internal surface extends beyond said portion,
   wherein the internal helical formation has a helix angle between 5 and 50 degrees relative to a longitudinal axis of the stent, and wherein the tubular member is selected from the group consisting of:
   (a) a tubular mesh member;
   (b) a tubular member formed from a wire; or
   (c) a tubular member of a mesh material that is formed from expanded sheet.

2. The stent according to claim 1, wherein the tubular member is expansible and is inserted by catheterization in collapsed form and which becomes expanded on release from the catheter, the internal helical formation being attached to the portion of the internal surface of the tubular member.

3. The stent according to claim 1, wherein the tubular mesh member is formed from a wire and comprises crisscrossed wires extending helically around the periphery of the stent, and the internal helical formation comprises a helical vane member attached to such wires.

4. The stent according to claim 1, wherein the tubular mesh member, the wire or the expanded sheet is made from metal.

5. The stent according to claim 1, wherein the wire is a wire spring.

6. The intravascular stent according to claim 1, wherein the helix angle is between 5 and 16 degrees relative to the longitudinal axis of the tubular member.

7. The intravascular stent according to claim 6, wherein the helix angle is about 16 degrees relative to the longitudinal axis of the tubular member.

8. The intravascular stent according to claim 1, wherein the helix angle of the internal helical formation is adjustable.

9. The intravascular stent according to claim 1, wherein the internal helical formation is a ridge.

* * * * *